United States Patent
Esty

(10) Patent No.: US 9,427,411 B2
(45) Date of Patent: Aug. 30, 2016

(54) OXYGENATED ANTIMICROBIAL TOPICAL COMPOSITION

(71) Applicant: JoAnna M. Esty, Middle River, MD (US)

(72) Inventor: JoAnna M. Esty, Middle River, MD (US)

( * ) Notice: Subject to any disclaimer, the term of this patent is extended or adjusted under 35 U.S.C. 154(b) by 0 days.

(21) Appl. No.: 14/457,605

(22) Filed: Aug. 12, 2014

(65) Prior Publication Data

US 2015/0044299 A1 Feb. 12, 2015

Related U.S. Application Data

(60) Provisional application No. 61/865,123, filed on Aug. 12, 2013.

(51) Int. Cl.
| | |
|---|---|
| *A61K 33/38* | (2006.01) |
| *A61P 31/04* | (2006.01) |
| *A61K 9/51* | (2006.01) |
| *A61K 47/02* | (2006.01) |
| *A61K 33/40* | (2006.01) |

(52) U.S. Cl.
CPC .............. *A61K 9/5107* (2013.01); *A61K 33/38* (2013.01); *A61K 33/40* (2013.01); *A61K 47/02* (2013.01)

(58) Field of Classification Search
None
See application file for complete search history.

(56) References Cited

U.S. PATENT DOCUMENTS

| | | | | |
|---|---|---|---|---|
| 2001/0055622 | A1* | 12/2001 | Burrell | A61K 33/24 424/600 |
| 2011/0262556 | A1* | 10/2011 | Holladay | A01N 59/16 424/616 |

* cited by examiner

*Primary Examiner* — H. Sarah Park

(57) ABSTRACT

The present invention relates to an antimicrobial topical composition and process for making such composition. The composition comprises of ionic silver, silver nanoparticles, and oxygen, combined within a gel medium and applied topically. The composition optimizes the ionic silver and silver nanoparticle ratio providing for sufficient ionic silver to be delivered as an immediate antimicrobial agent, and sufficient nanoparticle silver to provide time release for conversion to silver ions for continuing antimicrobial effectiveness.

3 Claims, 2 Drawing Sheets a. Silver nanoparticle colloidal solution comprising of water (H$_2$O), silver ions (Ag$^+$) and silver nanoparticles (Ag).

b. Silver nanoparticle colloidal solution is gelled.

c. Hydrogen peroxide is added and the gel composition is isolated and stored d. The hydrogen peroxide ionizes silver and released oxygen (O$_2$) is trapped in gel.

OXYGENATED ANTIMICROBIAL TOPICAL COMPOSITION

CROSS REFERENCES TO OTHER APPLICATIONS

This application claims priority from U.S. Provisional Application 61/865,123, filed Aug. 12, 2012, and this application is incorporated by reference herein in its entirety.

FIELD OF INVENTION

This invention relates to antimicrobial compositions and processes for making such compositions that can be used in the treatment and prevention of infection and diseases.

BACKGROUND OF THE INVENTION

There are a variety of diseases which can debilitate humans and animals, including bacterial infections, viral infections, fungal infections and parasites. Science and medicine are continually searching for better and more effective methods and compositions for curing or alleviating these diseases and their associated effects. Many times, the diseases can develop in concert with each other, one pathogen attacking one part of the subject while a separate pathogen attacks another. Unfortunately, many treatments are very disease or pathogen dependent and not all treatments are effective.

Antibiotics have been in use for almost a century to fight bacterial infections. Over time, antibiotics are losing the fight against bacteria. Production of new antibiotics has not kept up with the ability of bacteria to adapt and become resistant. Alternatives to antibiotics are desirable and necessary to fight harmful pathogens. Bacteria strains that are resistant to antibiotics are on the increase. Research continues in an effort to keep up with and discover new and effective therapeutic compositions and methods which can be used in the treatment of a variety of diseases and disorders.

Silver is known to be antimicrobial. It is effective and non-toxic when used in small quantities. Silver has been shown to have antibacterial, antiviral and antifungal properties. It is believed that the silver ions disrupt the respiratory functions or other functions of single-celled bacterial microorganisms, and may also disrupt membrane functionality or link to the cell's DNA. Silver is known to have antimicrobial effects on over 650 disease-causing germs. The present invention is harmless to the body when used in the low quantities needed for the antimicrobial action to occur, especially since the formulation provides an efficiently controlled, gradual release of free silver ions.

A major drawback when using silver as against pathogens, however, is that the larger particle silver cannot necessarily all be processed and expelled by the body, and excess silver can collect in the pigment of the skin. This excess silver causes a cosmetic condition called argyria, where the skin has a bluish tinge.

Recent technology developments now make it possible to manufacture nanoparticles of silver, as well as silver ions, in solution. Although bacteria can be controlled with larger particle silver, larger particle silver does not seem to be effective against viruses. Silver nanoparticles of ten (10) nanometers and smaller have been shown to exhibit similar antimicrobial properties as silver ions, particularly with respect to viruses. For viruses, it is believed that the silver nanoparticles (and/or the silver ions) disrupt the ability of the virus to bind to cell receptor sites.

Particle surface area contact affects the efficacy of the silver against pathogens. The greater the silver particle surface area in contact with a pathogen, the better the antimicrobial properties seem to be. As silver particle size decreases, the surface area of a quantity of silver particles increases. A quantity of smaller particle silver of, for example, the nanometer size, has much more surface area than larger particles of silver of the same quantity. As a result, the same amount of large particle silver has much less effectiveness against pathogens as a much smaller amount of nanoparticles; that is, to obtain the same surface area as larger particles of silver, much less nanoparticle silver is necessary. Smaller quantities of nanoparticle silver can be used to obtain the same desired surface area so that the total amount of silver used is well below the threshold of that which would cause argyria.

During recent years, materials containing silver have shown a substantial increase in popularity. Those containing silver ions and silver nanoparticles are increasingly regarded as a reasonably safe and effective antimicrobial agent.

Delivering bioavailable silver ions for utilization on the body is a challenge because silver ions are electrically attracted to a host of substances on the body. Silver ions in contact with the body will rapidly form complexes or compounds with other materials in the air and on or in the body, and these complexes or compounds will not have the antimicrobial properties of the silver ions, resulting in the silver ion becoming unavailable to perform the appropriate topical Silver ions are on the increase use in medical applications, particularly as a natural alternative to traditional antibiotics. Ionic silver is being used in topical dressings to treat wounds and to prevent and treat infections and contamination from harmful pathogens. However, these topical dressings have their drawbacks and shortcomings.

If silver ions are used topically and they are not shielded (or part of a bioactive particle, complex or compound), there is only a brief opportunity for them to perform the antimicrobial function—where and when they make contact with the body. Because of their high reactivity, the ions are reacted almost immediately with any topical application. Thus, topical formulations containing silver ions may be initially highly antimicrobial, but as the silver ions quickly react, the topical formulation loses its antimicrobial properties and becomes ineffective.

Various silver-containing chemical substances have been also been tried and used in the past in an effort to gain a sustaining antimicrobial benefit, but these substances too have generally proven to be minimally effective in or on the body because they also immediately deliver all of their silver content as free silver ions—silver ions that combine with other substances to lose their antimicrobial properties. Examples include U.S. Pat. No. 3,761,590 (complexes the silver ion to the antibiotic sulfadiazine to form silver sulfadiazine, a form of silver salt); U.S. Pat. No. 4,906,466 (complexes silver ions to titanium oxide; U.S. Pat. Nos. 5,429,819 and 6,093,414 (utilizes silver thiosulfate ion complexes). As well, some of these substances, such as silver nitrate, are undesirably toxic to the human body when administered in typical doses.

To avoid the immediate exhaustion of the topically applied silver ions, it is desirable to develop a way of delivering silver ions over time.

BRIEF DESCRIPTION OF THE INVENTION

The instant invention addresses the need for antimicrobial topical product that has both immediately bioavailable silver ions to kill pathogens, and additionally provide for the time release of silver ions, so that the topical formulation continues to be effective over time against harmful microbes. Additionally, the instant invention provides silver in a form that provides bactericide, viricide, fungicide and other antimicrobial properties. Many existing formulations include silver ions suspended in a gel, lotion or other medium for delivery topically. These topically delivered silver ions are immediately bioavailable to kill pathogens, and are only somewhat shielded from reaction by the gel. Since the gel has limited encapsulation of the silver ions, and the silver ions are so reactive, as the gel dries, the silver ions react quickly and have no capacity to remain active over time.

In order to deliver bioavailable silver topically both immediately and over time, an optimized blend of silver ions and silver nanoparticles is necessary. Silver nanoparticles are much less reactive than silver ions. Unlike silver ions, silver nanoparticles are stable and relatively inert, and will not rapidly be consume, or react to form other non-antimicrobial complexes or compounds. Over time, the silver nanoparticles do exhibit similar antimicrobial properties as silver ions. Presumably, the silver atoms on the surface of the silver nanoparticles exhibit properties similar to silver ions.

Most colloidal silver on the market today contain ionic silver rather than nanoparticle silver. These solutions are clear because the silver ions are dissolved in water. These solutions contain little, if any, silver nanoparticles—typically less than ten percent (10%). These colloidal silvers are used as the active ingredient in the topical silver products on the market today. Examples of these products are ASAP Colloidial Silver and Sovereign Silver. Because these products start with a solution of highly ionic silver, the topical products made from them are highly concentrated in silver ions, with little, if any, silver nanoparticles. Consequently the ratio of silver ions to silver nanoparticles cannot be easily changed or optimized from what it is. Containing very little nanoparticle silver, the ratio of silver ions to silver nanoparticles is usually greater than 9:1. To provide for time release of silver ions the present invention, the silver ion to silver nanoparticle ratio should be less than 9:1 and approaching 1:1 or even less (e.g., as low as 1:9). With a 1:1 ratio or even as low as a 1:9 ratio, there are sufficient silver ions to provide immediate bactericide effects, and the silver nanoparticles are available to act as an antimicrobial, providing time release of silver ions.

It is well known that skin cells repair and heal faster in an oxygen rich environment. When skin cells are compromised due to any pathogen activity, the skin cells benefit from contact with oxygen. The present invention teaches oxygenating the topical silver composition. Having a formulation that contains ionic silver and nanoparticle silver in an optimized ratio to provide antimicrobial activity over time, as well as an oxygenated formulation, significantly benefits the affected areas.

The present invention relates to stabilized compositions having antibacterial, antiviral and/or antifungal activity.

The invention relates to a method of producing compositions having antibacterial, antiviral and/or antifungal activity.

The invention also relates to the use of the stabilized compositions having antibacterial, antiviral and/or antifungal activity for wounds, burns, skin abrasion, skin irritations and skin inflammations (such as acne and the like).

Accordingly, the use of an optimized ratio of silver ions and silver nanoparticles is desirable for achieving appropriate topical antimicrobial silver formulation in order to obtain the benefits of the increase reactivity of the silver ion, and the over time, longer lasting continued antimicrobial effectiveness of the topical silver nanoparticles.

It is an object of the invention to topically provide the desirable characteristics of an antimicrobial ionic silver.

It is another object of the invention to provided nanoparticle silver that continues over time to be bioavailable as an antimicrobial.

It is an object of the present invention to provide a formulation of silver ions and silver nanoparticles that is stable against loss of the antiseptic activity over time.

It is a further object of the invention to deliver encapsulated oxygen with ionic silver in a topical delivery medium, such as a gel.

It is a further object of the invention to deliver encapsulated oxygen with nanoparticle silver in a topical delivery medium, such as a gel.

It is a further object of the invention to deliver encapsulated oxygen with ionic silver and nanoparticle silver in a topical delivery medium, such as a gel.

It is a further object of the invention to provide an oxygenated gel that provides oxygen to an affected area.

Additional features and advantages of the invention will be apparent from the detailed description that follows, which illustrates, by way of example, features of the invention.

FIGURES

DETAILED DESCRIPTION OF THE INVENTION

The present invention relates to products and methods for treatment and prevention of viral infections, bacterial infections, fungal infections and the like.

The description of the invention is divided into the following parts: I) Silver Nanoparticle Colloidal Solution, II) Gelling The Silver Nanoparticle Colloidal Solution, and III) Ionization Of Silver And Oxygenation Of The Gel Composition.

Figure 1:
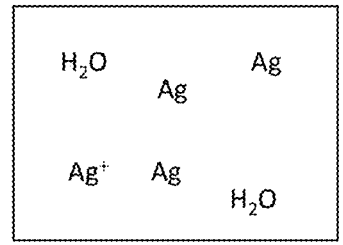
FIG. 1 illustrates the process of making antimicrobial composition.
Figure 1:
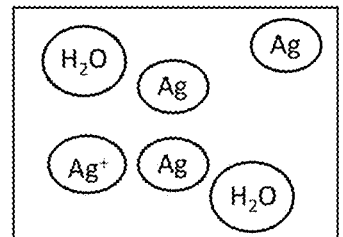
Figure 1:
Figure 1:
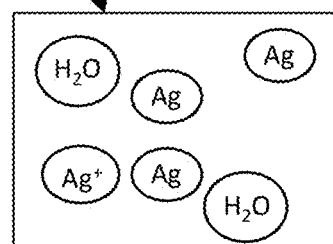
Figure 1:
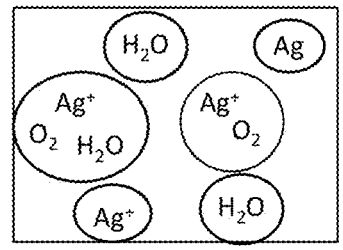

I. Silver Nanoparticle Colloidal Solution. In the first step of making the present invention, a solution of purified water, or water and other non-reactive ingredients, containing highly concentrated nanosilver particles (more than fifteen percent (15%) of the silver in a solution is silver nanoparticles) is used. If only water is used with the silver, the solution is known as a silver nanoparticle colloidal solution (see FIG. 1). The solution has a brownish color that may vary from light brown to a dark brown, reflecting the percentage of nanoparticles in the solution. A high percentage of silver nanoparticles at a higher concentration of silver will have a darker color. A lower percentage of silver nanoparticles with a lower concentration will have a lighter color. To avoid undesirable side reactions it is important to use such solutions that do not contain undesirable impurities or toxins. The initial water-based solution can be purchased at approx. 150 ppm from manufacturers such as Purest Colloids, Inc. Westampton, N.J. It can then be diluted with purified water or other non-reactive ingredients.

Silver concentrations of above 25 ppm in the silver nanoparticle colloidal solution are optimum to assure antimicrobial effectiveness. The aqueous compositions used in the methods of the present invention can be incorporated with other ingredients.

II. Gelling The Silver Nanoparticle Colloidal Solution. The addition of the carbomer or gelling agent to the silver causes the encapsulation of the silver ions and silver nanoparticles. For the gelling agents, examples of gelling or thickening agents include but are not limited to natural gum, a carbomer, cellulose, a cellulose derivative, and the like that form a barrier around the silver nanoparticles. The gelled composition will take on the color of the silver nanoparticle solution, which varies from light brown to dark brown based on silver ion to silver nanoparticle ratio and silver concentration.

The resulting gel composition has approximately the same silver concentration and silver ratios as the silver nanoparticle colloidal solution that was used. It can have a silver concentration of between 15 to 200 ppm and a silver nanoparticle to silver ion ratio of between 15 to 100% silver nanoparticles with the remaining silver being silver ions.

III. Ionization Of Silver And Oxygenation Of The Gel Composition. To optimize the silver ion to silver nanoparticle ratio, and to oxygenate the gel composition, hydrogen peroxide is added. This is shown in FIG. 1c. Hydrogen peroxide ionizes silver. The reaction of hydrogen peroxide in the presence of silver is:

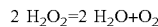

Oxygen is liberated and silver is ionized:

By mixing the gel composition with hydrogen peroxide, the ratio of silver ions to silver nanoparticles can be adjusted to increase the number of silver ions. At the same time, the ionization of the silver causes the liberation of oxygen gas. The liberated oxygen gas is trapped in the gel, causing the oxygenation of the gel composition.

For small amounts of oxygenation, only a small amount of silver is ionized. For greater amounts of oxygen, more silver ions are formed. At concentrations of silver of 30 ppm, at a ratio of 1:1 of silver ions to silver particles, the gel composition also will turn clear, indicating that the amount of silver ions has increased.

When the hydrogen peroxide is added to the gel compound there is no immediate visible change in the color of the gel composition. Because of the barrier created by the encapsulating gel substance, this color change, and accordingly, the silver ionization and hydrogen peroxide reaction occur over time as the hydrogen peroxide has time to infuse the gel and come into contact with the silver nanoparticles. To insure that the oxygen is kept within the gel composition, the hydrogen peroxide is mixed gently into the gel and then the gel compound is covered. The infusing and reacting of the hydrogen peroxide and silver occur over time as the hydrogen peroxide contacts the silver within the gel. This curing process may take from several hours to several days to be fully complete depending on the silver concentrations and ratios, and on the concentration of hydrogen peroxide used. In a preferred embodiment, a low percentage of hydrogen peroxide is optimum, such as 4%, because greater concentrations are much more reactive and can cause the reaction to occur too quickly, which may be hazardous.

In FIG. 1d there is shown the composition of the gel composition after addition of the hydrogen peroxide and time to cure. The oxygen is liberated and water is released, with the silver being ionized. The ratio of silver ions to silver nanoparticles has increased as well, making the topical application more immediately reactive, and having sufficient silver nanoparticle concentration to continue reacting over time. That is, the silver nanoparticles are encapsulated and are stable, and react as an antimicrobial much more slowly.

Although different concentrations at different silver to nanoparticle ratios can be used, a concentration of at least 30 ppm of silver with a 1:1 silver ion to silver nanoparticle ratio has good initial antimicrobial properties, and also provides an effective time release of silver also having antimicrobial properties.

Once the gel is cured it can be used topically to treat bacterial, viral infection and fungal infections. It can comprise administering the gel topically to the subject in an amount sufficient to prevent or treat the bacterial infection. In another embodiment, it comprises administering the gel topically to the subject in an amount sufficient to prevent or treat the viral infection. In a further embodiment, it comprises administering the gel topically to the subject in an amount sufficient to prevent or treat the viral infection. In a further embodiment, each of these embodiments, whether treatment is as a prophylactic or to ameliorate the disease or injury after infection, the composition can comprise an topical vehicle, such as a gel, including silver ions and silver nanoparticles from 15% concentration of silver nanoparticles to 100%, in total silver concentrations of 15 ppm to 200 ppm and greater as may be desirable for treatment, with entrained oxygen provided to the subject's affected area to aid with healing.

Figure 2:
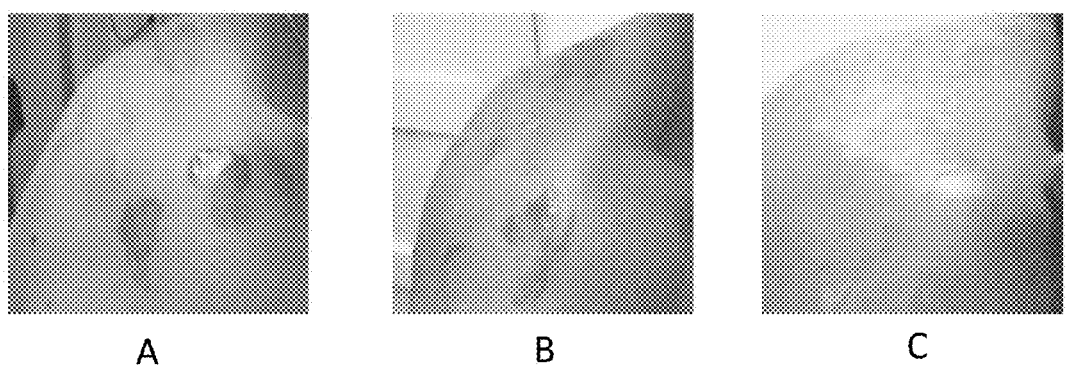
FIG. 2 shows the efficacy of the gel product in photographs of a topical application applied over time to a patient with tinea versicolor and ring worm.

As shown in FIGS. 2, an application of the topical gel of the present invention was applied to a patient having tinea versicolor and ring worm. Applications were continued over time, with FIG. 2b showing the effect of the topical gel on the microbially affected area after approximately 4 hours, and FIG. 2c showing the effect after approximately 24 hours. Notably, the patient continued to use the topical gel over the next 72 hours to fully eradicate the microbes.

The compositions of the invention may be e.g. used in wound dressings. In particular the gel is suitable for incorporating with dressings. The compositions of the invention and formulations thereof may be used for antibacterial, antiviral or antifungal use in the area of human or veterinary medicine.

Concentrations, dimensions, amounts, and other numerical data are presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited.

The following example illustrates an embodiment of the invention that is presently best known. However, it is to be understood that the following is only exemplary or illustrative of the application of the principles of the present invention. Numerous modifications and alternative compositions, methods, and systems may be devised by those skilled in the art without departing from the spirit and scope of the present invention. While the present invention has been described above with particularity, the following examples provide further detail in connection with what are presently deemed to be the most practical and preferred embodiments of the invention.

Antimicrobial Gel Composition

A gel composition is prepared using approx. 30 ppm a silver nanoparticle colloidal solution having 10% silver ions and 90% silver nanoparticles from Purest Colloids, Inc. Sodium Carbomer sufficient to gel the silver nanoparticle colloidal solution is added. The gel composition is moved to a mixing and storage container, provided with a mechanism for sealing it after addition of the 4% solution hydrogen peroxide. The hydrogen peroxide is added to the gel and slowly mixed into it. A sufficient quantity of hydrogen peroxide is added to permit the ionization of silver nanoparticles sufficient to increase the percentage of silver ions to approx. 50%. This range may vary depending on the desired ratio of silver ions to silver nanoparticles. After mixing, the gel composition is covered and stored for curing for a sufficient time to allow the hydrogen peroxide to penetrate the gel barrier surrounding each silver nanoparticle, causing the hydrogen peroxide to react to form water and oxygen gas, and causing the silver nanoparticle to be ionized.

When the cured gel is used topically, the silver ions contacting bacteria will have immediate bactericide affects. The silver nanoparticles will remain topically, and over time will release silver ions for continued effectiveness.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

The product can be used for humans as well as animals. Thus, the invention has a wide range of potential uses for both medical and veterinary applications.

The invention claimed is:

1. A topical antimicrobial composition comprising a total concentration of silver of between 15-200 parts per million, comprising (i) silver ions and silver nanoparticles, wherein the ratio of silver ions to silver nanoparticles is between 1:1-1:9, (ii) oxygen, and (iii) a gelling agent, wherein the oxygen is captured and held within the gelling agent.

2. The composition according to claim 1, wherein the oxygen concentration is between 3% wght/v to 10% wgt/v.

3. The composition according to claim 1, wherein the gelling agent comprises of sodium carbomer.

* * * * *